(12) United States Patent
Ohnishi

(10) Patent No.: US 7,087,044 B2
(45) Date of Patent: Aug. 8, 2006

(54) ABSORBENT ARTICLE

(75) Inventor: Kazuaki Ohnishi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 93 days.

(21) Appl. No.: 10/704,125

(22) Filed: Nov. 10, 2003

(65) Prior Publication Data

US 2005/0055000 A1    Mar. 10, 2005

(30) Foreign Application Priority Data

Nov. 12, 2002 (JP) .............................. 2002-327971

(51) Int. Cl.
*A61F 13/20* (2006.01)
(52) U.S. Cl. .................. 604/385.01; 604/378
(58) Field of Classification Search ........... 604/385.01, 604/378
See application file for complete search history.

(56) References Cited

U.S. PATENT DOCUMENTS

| | | | | |
|---|---|---|---|---|
| 4,676,786 A | * | 6/1987 | Nishino | ...... 604/378 |
| 4,692,163 A | | 9/1987 | Widlund et al. | |
| 4,775,375 A | * | 10/1988 | Aledo | ...... 604/378 |
| 4,840,692 A | * | 6/1989 | Kamstrup-Larsen | ...... 156/252 |
| 4,847,134 A | * | 7/1989 | Fahrenkrug et al. | ...... 428/138 |
| 4,891,258 A | * | 1/1990 | Fahrenkrug | ...... 428/138 |
| 6,488,670 B1 | * | 12/2002 | Schild et al. | ...... 604/385.24 |

FOREIGN PATENT DOCUMENTS

| | | |
|---|---|---|
| EP | 0 321 985 | 6/1989 |
| EP | 1057464 A2 * | 6/2000 |
| EP | 1 116 479 | 7/2001 |
| JP | 11-99170 | 4/1999 |
| JP | 11-99171 | 4/1999 |
| JP | 11-299827 | 11/1999 |
| JP | 2000-354601 | 12/2000 |
| WO | WO91 09580 | 7/1991 |

* cited by examiner

*Primary Examiner*—Tatyana Zalukaeva
*Assistant Examiner*—Ginger Chapman
(74) *Attorney, Agent, or Firm*—Lowe Hauptman Berner LLP

(57) ABSTRACT

An absorbent article has a top sheet, a back sheet, and an absorbent body. The absorbent body has an intermediate sheet, a first absorbent body group, a second absorbent body group, and a stretchable member having stretchability to shrink the intermediate sheet, first absorbent body group, and second absorbent body group in a transverse direction. Each of the absorbent body groups has a plurality of strip-shaped absorbent bodies that extend in a longitudinal direction. The strip-shaped absorbent bodies are disposed at predetermined intervals.

19 Claims, 3 Drawing Sheets

ABSORBENT ARTICLE

CROSS-REFERENCE TO RELATED APPLICATIONS

This application is based upon and claims the benefit of priority from the prior Japanese Patent Application No. 2002-327971 filed on Nov. 12, 2002, the entire contents of which is incorporated herein by reference.

FIELD OF THE INVENTION

The present invention relates to an absorbent article, such as a diaper, incontinence pad, menstrual napkin, etc., which is worn by a wearer and absorbs and retains body fluids of the wearer.

BACKGROUND OF THE INVENTION

Conventionally, absorbent articles, which are worn by a wearer for the purpose of absorbing and retaining body fluids of the wearer, have been known. Such an absorbent article comprises a surface side sheet which allows the permeation of the body fluids, a back face side sheet which does not allow the permeation of the body fluids, and an absorbent body which is disposed between the abovementioned sheets. With the absorbent article, body fluids are absorbed and retained by the absorbent body so as to prevent the leakage of the body fluids to outside through the back face side sheet.

The part of the above-described absorbent article which is fitted to the crotch of a wearer must be narrow in width to make the wearer comfortable. The absorbing ability of the absorbent article is thereby lowered.

Also, the width of the absorbent article changes due to movements of the wearer, and this causes kinking, twisting, etc., of the absorbent article. It was thus difficult to fit the absorbent article to the crotch of the wearer to make the wearer comfortable.

In order to solve the problems, the following absorbent article has been proposed (refer to Japanese Unexamined Patent Publication No. 2000-354601). That is, an absorbent article includes a surface side sheet, a back face side sheet joined to the surface side sheet, and an absorbent body interposed between the surface side sheet and the back side sheet. Central parts in the lengthwise direction of the surface side sheet and the absorbent body have bellows-like cross-sectional shapes, and the back face side sheet is laminated onto the absorbent body of the bellows-like shape.

With this arrangement, the surface side sheet and the absorbent body expand and shrink to follow the movements of a wearer, so that the length in the width direction of the absorbent article changes. The kinking and twisting of the absorbent body can thereby be prevented not to make the wearer uncomfortable.

The above-described absorbent article is manufactured by the following method. That is, a surface side sheet and a absorbent are laminated and then press-formed to a bellows-like shape by a rotating drum, and thereafter, a back face side sheet is laminated onto the absorbent body. Therefore, by the press-forming, the absorbent body tended to harden and the absorbent body could become high in density to decrease absorbing ability.

SUMMARY OF THE INVENTION

The present invention has been made in view of such problems of the background art and an object thereof is to provide an absorbent article which is able to maintain absorbing ability without decreasing comfort of a wearer.

More specifically, the present invention provides the following.

(1) An absorbent article for being worn by a wearer to absorb and retain body fluids of the wearer, comprising: a surface side sheet allowing the permeation of the body fluids; a back face side sheet joined to said surface side sheet and not allowing the permeation of the body fluids; an absorbent body interposed between said surface side sheet and said back face side sheet; wherein said absorbent body including an intermediate sheet, first absorbent body group provided on a surface side sheet side of said intermediate sheet, second absorbent body group provided on a back face side sheet side of said intermediate sheet, and a stretchable member having stretchability to shrink said intermediate sheet, said first absorbent body group, and said second absorbent body group in a transverse direction; and wherein each of said absorbent body groups has a plurality of strip-shaped absorbent bodies to extend in a longitudinal direction, the strip-shaped absorbent bodies disposed at predetermined intervals.

The absorbent article can be used favorably as a diaper, continence pad, menstrual napkin, etc.

With the invention of (1), an absorbent body includes an intermediate sheet, first absorbent body group disposed at a surface side sheet side of the intermediate sheet, second absorbent body group disposed at a back face side sheet side of the intermediate sheet, and a stretchable member having stretchability to shrink the intermediate sheet, first absorbent body group, and second absorbent body group in a transverse direction. Since the stretchable member shrinks to narrow the width of the absorbent article, the absorbent article can be fitted to a wearer to maintain comfort of the wearer.

Also, since each of the absorbent body groups has a plurality of strip-shaped absorbent bodies which extend in a longitudinal direction and these strip-shaped absorbent bodies are disposed at predetermined intervals, when the stretchable member shrinks, the intermediate sheet becomes bellows-like in shape and the strip-shaped absorbent bodies of the first absorbent body group and the second absorbent body group are gathered together and increase in specific weight. The absorbing ability per unit area of each of the absorbent bodies can thus be increased. Also, body fluids of a wearer flow along grooves between the respective strip-shaped absorbent bodies and become spread in the longitudinal direction of the absorbent article. The absorbing ability of each of the absorbent body group can thus be maintained.

Also, even when the dimension in the transverse direction of the absorbent article changes due to movements of the wearer, since the mutual intervals between the strip-shaped absorbent bodies change to follow the change of the dimension of the absorbent article, kinks and twists will not occur in the strip-shaped absorbent bodies. The absorbent article can follow the movements of the wearer surely.

Also, since an intermediate sheet is provided, flexibility and rigidity of the absorbent article can be secured.

(2) The above-described absorbent article, wherein the mutual intervals between the strip-shaped absorbent bodies in at least one of said first absorbent body group and said second absorbent body group are large.

With the invention of (2), since the mutual intervals between the strip-shaped absorbent bodies are large, even when the absorbent article is considerably narrowed in a transverse direction due to shrinking of the stretchable member, kinking and twisting of the strip-shaped absorbent bodies can be prevented so as not to lower comfort of wearer. Also, even if a large amount of body fluids are excreted at a high rate, since the grooves at the mutual intervals between the strip-shaped absorbent bodies are wide, the body fluids can be spread surely. The absorbing ability of the absorbent article can thus be maintained.

(3) The above-described absorbent article, wherein said intermediate sheet allows the permeation of the body fluids.

With the invention of (3), since an intermediate sheet which allows the permeation of the body fluids is provided, body fluids of a wearer can be flow surely to the second absorbent body group.

(4) The above-described absorbent article, wherein said stretchable member is disposed at substantially the center in the longitudinal direction of said intermediate sheet, and said intermediate sheet supports said stretchable member at the surface of said back face side sheet.

With the invention of (4), the stretchable member is disposed at substantially the center in the longitudinal direction of the intermediate sheet, and the intermediate sheet supports the stretchable member at the surface of the back face side sheet. That is, the stretchable member is supported at a plurality of points by the intermediate sheet, which is exposed from the mutual intervals between the strip-shaped absorbent bodies of the back face side sheet. The intermediate sheet, the first absorbent body group, and the second absorbent body group can thus be shrunk definitely in the transverse direction. Also, the intermediate sheet can be made bellows-like in shape surely when the stretchable member shrinks.

(5) The above-described absorbent article, wherein said intermediate sheet supports said stretchable member at parts of the surface of said back face side sheet corresponding to the back faces of said first absorbent body group.

The invention of (5) provides the effects similar to those of the invention of (4).

(6) The above-described absorbent article, wherein said stretchable member is positioned at a crotch of the wearer when said absorbent article is worn by the wearer.

Kinks and twists tend to be form readily at a crotch part of the absorbent article due to movements of a wearer. Thus with the invention of (6), the stretchable member is positioned at a crotch of the wearer when the absorbent article is worn by the wearer.

The absorbent article can thus be fitted to the crotch of the wearer and can absorb and hold body fluids of the wearer surely without lowering comfort of the wearer.

(7) The above-described absorbent article, wherein said stretchable member is formed integral with said back face side sheet.

Here, the back face side sheet may includes a resin with elasticity, for example, a polyolefin, polyurethane, styrene elastomer copolymer, etc., as a main component.

(8) The above-described absorbent article, further comprising: leak-proof gathers disposed upright along both edges in a transverse direction of said surface side sheet.

With the invention of (8), since leak-proof gathers are disposed upright along both edges in a transverse direction of the absorbent article, leakage of body fluids through the edges of the absorbent article can be prevented surely.

(9) The above-described absorbent article, wherein the absorbent article is a disposable diaper.

(10) A method for manufacturing an absorbent article, the absorbent article to be worn by a wearer to absorb and retain body fluids of the wearer, wherein the absorbent article includes a surface side sheet allowing the permeation of the body fluids, a back face side sheet joined to the surface side sheet and not allowing the permeation of the body fluids, and an absorbent body interposed between the surface side sheet and the back face side sheet, the absorbent body including an intermediate sheet, first absorbent body group provided on a surface side sheet side of the intermediate sheet, second absorbent body group provided on a back face side sheet side of the intermediate sheet, and a stretchable member having stretchability to shrink the intermediate sheet, the first absorbent body group, and the second absorbent body group in a transverse direction, wherein each of the absorbent bodies have a plurality of strip-shaped absorbent bodies to extend in a longitudinal direction, the strip-shaped absorbent bodies disposed at predetermined intervals, said method comprising the steps of: attaching a plain continuous absorbent member to the intermediate sheet; cutting parts of the continuous absorbent member at predetermined intervals to form the strip-shaped absorbent bodies.

With the invention of (10), the strip-shaped absorbent bodies are formed by attaching a plain continuous absorbent member to the intermediate sheet and thereafter cutting parts of the continuous absorbent member at predetermined intervals. Thus in comparison to a case where the respective strip-shaped absorbent bodies are cut out separately from a continuous absorbent member and the cut-out absorbent bodies are attached individually to the intermediate sheet, the process is simplified and the cost can be reduced.

DETAILED DESCRIPTION OF THE PREFERRED EMBODIMENT

An embodiment of the present invention will now be described by referring to the accompanying drawings.

Figure 1:
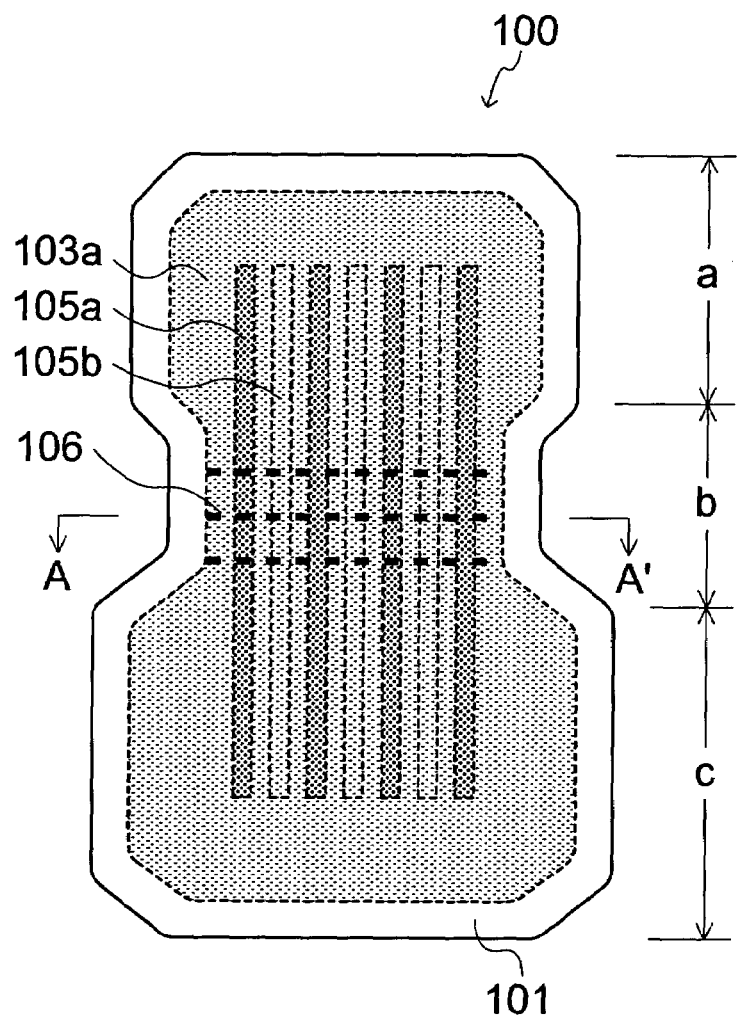
FIG. 1 is a plan view showing an absorbent article according to an embodiment of the present invention.
Figure 2:
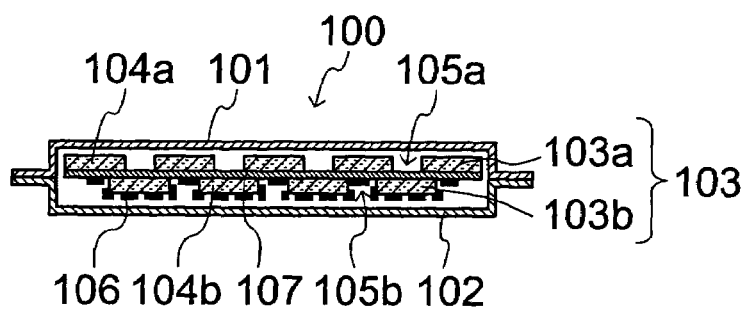
FIG. 2 is a sectional view through A–A' in FIG. 1.
Figure 3:
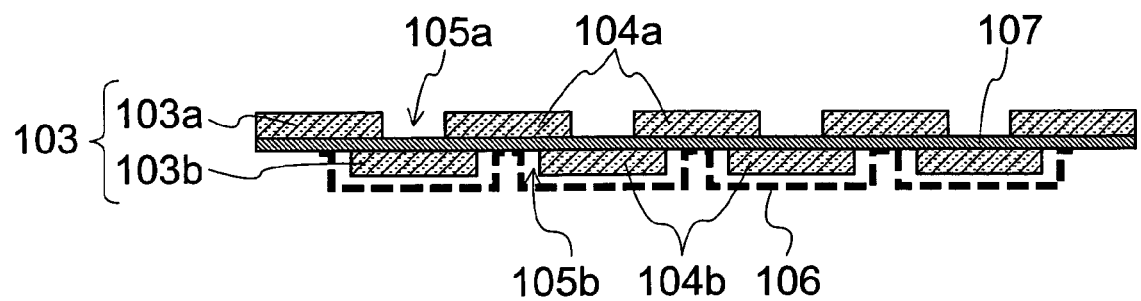
FIG. 3 is an enlarged sectional view through A–A' in FIG. 1.

FIG. 1 is a plan view showing an absorbent article according to an embodiment of the present invention. FIG. 2 is a sectional view through A–A' in FIG. 1. FIG. 3 is an enlarged sectional view through A–A' in FIG. 1.

An absorbent article 100 is worn by a wearer and absorbs and retains body fluids of the wearer. The absorbent article 100 has a crotch region b, provided at substantially the central part in the longitudinal direction and fitted to the crotch of the wearer, a lower abdominal region a, provided at one end side in the longitudinal direction and fitted to the lower abdominal part of the wearer, and a buttocks region c, provided at the other end side in the longitudinal direction and fitted to the buttocks of the wearer.

This absorbent article 100 has a surface side sheet 101, which allows the permeation of body fluids, a back face side sheet 102, which is joined to surface side sheet 101 and does not allow the permeation of body fluids, and an absorbent body 103, which is interposed between surface side sheet 101 and back face side sheet 102.

Also, though not shown, leak-proof gathers are disposed upright along both edges in a transverse direction of surface side sheet 101. These leak-proof gathers are made shrunk by an unillustrated stretchable rubber and fit to leg parts of a wearer.

Surface side sheet 101 is formed of a material having properties of hydrophile and non-irritation to skin. Specifically, the material of surface side sheet 101 includes a nonwoven fabric or nonwoven fabrics prepared by manufacturing methods, such as melt blowing, spun bonding, through air method, point bonding, needle punching, wet forming spun lacing, etc. Surface side sheet 101 is formed of such a nonwoven fabric or nonwoven fabrics by mixture.

Back face side sheet 102 has the property of not allowing the permeation of a body fluids to prevent the body fluids absorbed by absorbent body 103 from leaking to outside. The back face side sheet 102 may be formed of a moisture-permeable material to lower the humidity when absorbent article 100 is worn. The material of back face side sheet 102 includes a sheet-like film formed by forming a synthetic resin into a film, an air-permeable film obtained by filling inorganic filler and performing a drawing process, a paper, a laminate combining a nonwoven fabric and a film, and an air-permeable liquid-blocking sheet which has open pores with a pore diameter in the range of 0.1 to 0.6 mm at a porosity of 10 to 30% and capillary tubes disposed so as to be directed towards the absorbent body side.

Absorbent body 103 has an intermediate sheet 107, which allows the permeation of the body fluids, a first absorbent body group 103a, disposed at a surface side sheet 101 side of intermediate sheet 107, a second absorbent body group 103b, disposed at a back face side sheet 102 side of intermediate sheet 107, and a stretchable member 106, having stretchability to shrink intermediate sheet 107, first absorbent body group 103a, and second absorbent body group 103b in a transverse direction.

First absorbent body group 103a has a plurality of mutually-parallel, strip-shaped absorbent bodies 104a which extend in a longitudinal direction, and the mutual intervals between these strip-shaped absorbent bodies 104a define grooves 105a.

Second absorbent body group 103b has a plurality of mutually-parallel, strip-shaped absorbent bodies 104b which extend in a longitudinal direction and the mutual intervals between these strip-shaped absorbent bodies 104b define grooves 105b.

These strip-shaped absorbent bodies 104a, 104b are disposed alternately with respect to intermediate sheet 107. That is, a strip-shaped absorbent body 104a of first absorbent body group 103a and a groove 105b of second absorbent body group 103b interpose intermediate sheet 107 therebetween, and a groove 105a of first absorbent body group 103a and a strip-shaped absorbent body 104b of second absorbent body group 103b interpose intermediate sheet 107 therebetween.

First absorbent body group 103a and second absorbent body group 103b are formed by attaching a plain continuous absorbent to intermediate sheet 107 and then cutting parts of the continuous absorbent member at predetermined intervals to form grooves 105a, 105b.

The method for manufacturing first absorbent body group 103a and second absorbent body group 103b is not restricted to the above-described method and, for example, strip-shaped absorbent bodies may be disposed individually at predetermined intervals on the intermediate sheet.

Strip-shaped absorbent bodies 104a, 104b absorb and retain body fluids, etc. Preferably, strip-shaped absorbent bodies 104a, 104b are bulky, keep their shapes well, and are low in terms of chemical irritation. Examples of the material of strip-shaped absorbent bodies 104a, 104b include pulp, chemical pulp, rayon, acetate, natural cotton, absorbent polymer, absorbent polymer fibers, synthetic fibers, etc. Specifically, strip-shaped absorbent bodies 104a, 104b are formed of such a material or materials by mixture.

Stretchable member 106 is disposed between second absorbent body group 103b and back face side sheet 102 at crotch region b in a state which stretchable member 106 is stretched in a direction intersecting the direction of the extension of the strip-shaped absorbent bodies 104a, 104b.

Stretchable member 106 is supported by the back face side sheet 102 side surface of intermediate sheet 107 at grooves 105b of second absorbent body group 103b.

Also, stretchable member 106 is in contact with but is not attached to strip-shaped absorbent bodies 104b of second absorbent body group 103b.

Stretchable member 106 is not restricted in particular as long as it has stretchability. Examples of the material of stretchable member 106 include natural rubber, synthetic rubber, and polyurethane. Stretchable member 106 is formed of a thread-like rubber, flat rubber, ribbon-like elastic body, heat-stretchable material, or water-absorbent stretchable fibers made from an abovementioned material.

Intermediate sheet 107 is formed of a material having properties of hydrophile and allowance of permeation of body fluids, such as the same material as that of surface side sheet 101.

The actions of absorbent article 100 shall now be described with reference to FIGS. 4 to 7.

Figure 4:
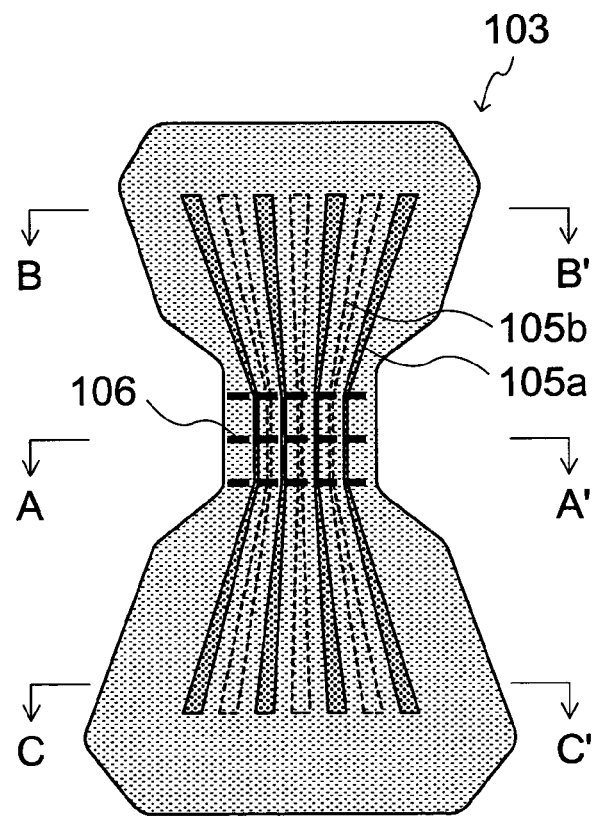
FIG. 4 is a plan view showing the absorbent article in a state where a stretchable member is shrunk according to the embodiment.
Figure 5:
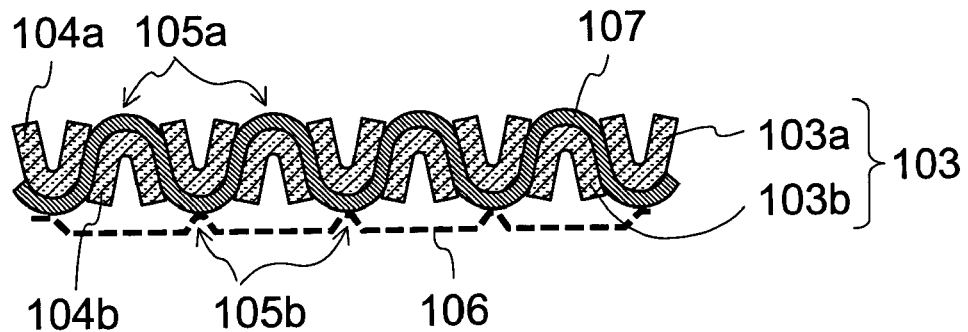
FIG. 5 is a sectional view through A–A' in FIG. 4.
Figure 6:
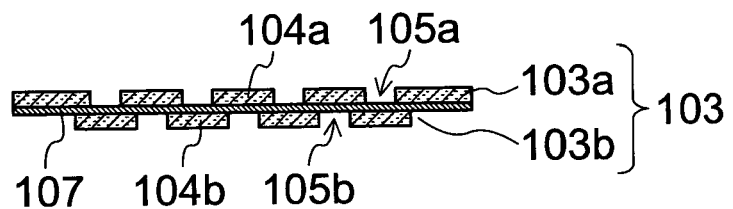
FIG. 6 is a sectional view through B–B' in FIG. 4.
Figure 7:
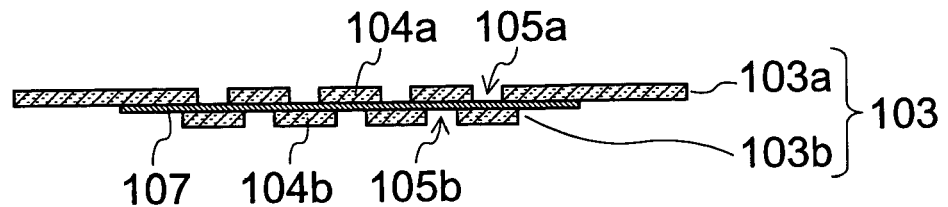
FIG. 7 is a sectional view through C–C' in FIG. 4.

FIG. 4 is a plan view showing the absorbent article in a state where the stretchable member is shrunk. FIG. 5 is a sectional view through A–A' in FIG. 4. FIG. 6 is a sectional view through B–B' in FIG. 4. FIG. 7 is a sectional view through C–C' in FIG. 4.

When stretchable member 106 shrinks, since this stretchable member 106 is attached at predetermined intervals to intermediate sheet 107, the dimensions between grooves 105b of second absorbent body group 103b to which stretchable member 106 is attached decrease as shown in FIG. 4. Intermediate sheet 107 thus becomes a bellows-like shape, and in accordance with this shape change, strip-shaped absorbent bodies 104a of first absorbent body group 103a and strip-shaped absorbent bodies 104b of second absorbent body group 103b transform to substantially V-like shapes. Crotch region b of absorbent article 100 thus becomes a bellows-like shape.

Since the width of absorbent article 100 thus becomes narrow due to the shrinkage of stretchable member 106, absorbent article 100 can be fit to the wearer surely without lowering comfort of wearer.

Also, when stretchable material 106 shrinks, intermediate sheet 107 becomes bellows-like in shape and strip-shaped absorbent bodies 104a, 104b of first absorbent body group 103a and second absorbent body group 103b are gathered together and increase in specific weight. The absorbing ability per unit area of each of absorbent body groups 103a, 103b can thus be increased. Also, body fluids of a wearer flow along grooves 105a, 105b between the strip-shaped absorbent bodies 104a, 104b and become spread in the longitudinal direction of absorbent article 100. The absorbing ability of each of absorbent body groups 103*a*, 103*b* can thus be maintained.

Also, even when the dimension in the transverse direction of absorbent article 100 changes due to movements of the wearer, since the mutual intervals between strip-shaped absorbent bodies 104*a*, 104*b* change to follow the change of the dimension of the article 100, kinks and twists will not occur in strip-shaped absorbent bodies 104*a*, 104*b*. The absorbent article 100 can follow the movements of the wearer surely.

Also, since intermediate sheet 107 is provided, flexibility and rigidity of the absorbent article can be secured.

The present invention is not limited to the above-described embodiment, and modifications, improvements, etc., within a range in which the objects of the present invention can be accomplished are included in the present invention.

For example, though with the above-described embodiment, strip-shaped absorbent bodies 104*a*, 104*b* are disposed alternately with respect to intermediate sheet 107, the present invention is not limited thereto, and strip-shaped absorbent bodies may instead be disposed at the same positions with respect to intermediate sheet.

Also, though with the present embodiment, stretchable member 106 is disposed between second absorbent body group 103*b* and back face side sheet 102, the present invention is not limited thereto, and for example, the stretchable member may instead be made integral with the back face side sheet.

Also, though with the present embodiment, just crotch region b of absorbent article 100 has a bellows-like shape, the present invention is not limited thereto, and the entirety of absorbent article 100 may have a bellows-like shape instead.

The absorbent article according to the present invention provides the following effects.

Since the stretchable member shrinks to narrow the width of the absorbent article, the absorbent article can be fitted closely to a wearer to maintain comfort of the wearer. Also, since each of the absorbent body groups has a plurality of strip-shaped absorbent bodies which extend in a longitudinal direction and these strip-shaped absorbent bodies are disposed at predetermined intervals, when the stretchable member shrinks, the intermediate sheet becomes bellows-like in shape and the strip-shaped absorbent bodies of the first absorbent body group and the second absorbent body group are gathered together and increase in specific weight. The absorbing ability per unit area of each absorbent body group can thus be increased. Also, body fluids of a wearer flow along grooves between the respective strip-shaped absorbent bodies and become spread in the longitudinal direction of the absorbent article. The absorbing ability of each absorbent body group can thus be maintained. Also, even when the dimension in the transverse direction of the absorbent article changes due to movements of the wearer, since the mutual intervals between the strip-shaped absorbent bodies change to follow the change of the dimension of the absorbent article, kinks and twists will not occur in the strip-shaped absorbent bodies. The absorbent article can follow the movements of the wearer surely. Also, since an intermediate sheet is provided, flexibility and rigidity of the absorbent article can be secured.

What is claimed is:

1. An absorbent article, comprising:
   a top sheet pervious to body fluids;
   a back sheet joined to said top sheet and impervious to the body fluids;
   an absorbent body interposed between said top sheet and said back sheet;
   said absorbent body including an intermediate sheet, a first absorbent body group provided on a top sheet side of said intermediate sheet, a second absorbent body group provided on a back sheet side of said intermediate sheet, and a stretchable member attached to said intermediate sheet to shrink said intermediate sheet, said first absorbent body group, and said second absorbent body group in a transverse direction of said article;
   wherein each of said first and second absorbent body groups has a plurality of strip-shaped absorbent bodies extending in a longitudinal direction of said article, the strip-shaped absorbent bodies in each of said first and second absorbent body groups being disposed at predetermined intervals in said transverse direction and spaced from each other by absorbent-free regions that are free of absorbent materials of said strip-shaped absorbent bodies; and
   wherein the strip-shaped absorbent bodies of said first absorbent body group are alternated with the strip-shaped absorbent bodies of said second absorbent body group with the strip-shaped absorbent bodies of said second absorbent body group being located corresponding to the absorbent-free regions between the strip-shaped absorbent bodies of said fast absorbent body group.

2. The absorbent article according to claim 1, wherein the intervals between the strip-shaped absorbent bodies in at least one of said first absorbent body group and said second absorbent body group are large.

3. The absorbent article according to claim 1, wherein said intermediate sheet is pervious to the body fluids.

4. The absorbent article according to claim 1, wherein said stretchable member is disposed in a longitudinally middle portion of said intermediate sheet.

5. The absorbent article according to claim 1, wherein said stretchable member is directly attached to said intermediate sheet in the absorbent-free regions between the strip-shaped absorbent bodies of said second absorbent body group.

6. The absorbent article according to claim 1, wherein said stretchable member is positioned in a crotch region of said absorbent article.

7. The absorbent article according to claim 1, wherein said stretchable member is formed integral with said back sheet.

8. The absorbent article according to claim 1, further comprising:
   risable leak-proof barriers disposed along edges of said top sheet.

9. The absorbent article according to claim 1, wherein the absorbent article is a disposable diaper.

10. A method of manufacturing an absorbent article, wherein the absorbent article includes a top sheet pervious to body fluids, a back sheet joined to the top sheet and impervious to the body fluids, and an absorbent body interposed between the top sheet and the back sheet, the absorbent body including an intermediate sheet, a first absorbent body group provided on a top sheet side of the intermediate sheet, a second absorbent body group provided on a back sheet side of the intermediate sheet, and a stretchable member having stretchability to shrink the intermediate sheet, the first absorbent body group, and the second absorbent body group in a transverse direction of said article, and wherein each of the first and second absorbent body groups has a plurality of strip-shaped absorbent bodies to extend in a longitudinal direction of said article, the strip-shaped absorbent bodies being disposed at predetermined intervals in said transverse direction, said method comprising the steps of:
attaching a planar continuous absorbent member to the intermediate sheet, and
cutting selected parts of the continuous absorbent member to form the strip-shaped absorbent bodies which are spaced from each other by absorbent-free regions that are free of absorbent materials of said absorbent member;
said cutting being performed such that the strip-shaped absorbent bodies of said first absorbent body group are alternated with the strip-shaped absorbent bodies of said second absorbent body group with the strip-shaped absorbent bodies of said second absorbent body group being located corresponding to the absorbent-free regions between the strip-shaped absorbent bodies of said first absorbent body group;
said method further comprising the step of directly attaching the stretchable member to said intermediate sheet.

11. The method according to claim 10, wherein said stretchable member is attached to said intermediate sheet in the absorbent-free regions between the strip-shaped absorbent bodies of said second absorbent body group.

12. The method according to claim 11, wherein said stretchable member is attached to said intermediate sheet only in the absorbent-free regions between the strip-shaped absorbent bodies of said second absorbent body group, without being directly attached to said strip-shaped absorbent bodies of said second absorbent body group.

13. The absorbent article according to claim 5, wherein said stretchable member extends between the strip-shaped absorbent bodies of said second absorbent body group and the back sheet, without being directly attached to said strip-shaped absorbent bodies of said second absorbent body group.

14. An absorbent article, comprising:
a top sheet pervious to body fluids;
a back sheet joined to said top sheet and impervious to the body fluids;
an absorbent body interposed between said top sheet and said back sheet;
said absorbent body including an intermediate sheet, an upper absorbent core above said intermediate sheet, a lower absorbent core below said intermediate sheet, and a stretchable member for shrinking said intermediate sheet and said upper and lower absorbent cores in a transverse direction of said article;
wherein at least one of said upper and lower absorbent cores comprises a plurality of raised portions alternated with a plurality of grooves in which a thickness of said absorbent core is less than in the raised portions, said raised portions and grooves extending in a longitudinal direction of said article; and
wherein said stretchable member is directly attached to said intermediate sheet.

15. The absorbent article according to claim 14, wherein said stretchable member is directly attached to said intermediate sheet in said grooves, without being directly attached to said raised portions.

16. The absorbent article according to claim 15, wherein said grooves are free of absorbent materials of said raised portions.

17. The absorbent article according to claim 14, wherein said stretchable member is attached to said intermediate sheet in said grooves.

18. The absorbent article according to claim 17, wherein each of said upper and lower absorbent cores comprises said raised portions and grooves; and the raised portions of said upper absorbent core are alternated with the raised pardons of said lower absorbent core, with the raised portions of said lower absorbent core being located corresponding to the grooves of said upper absorbent core.

19. The absorbent article according to claim 18, wherein a width of the raised portions of said lower absorbent core, as measured in the transverse direction, is greater than that of the corresponding grooves of the upper absorbent core.

* * * * *